(12) United States Patent
Lavoisier et al.

(10) Patent No.: US 10,870,733 B2
(45) Date of Patent: Dec. 22, 2020

(54) PROCESS FOR PREPARING AN ALGAL POWDER CONTAINING A REDUCED CONTENT OF PROTEINS, AND BIOPLASTIC COMPOSITION FORMULATED FROM SUCH A POWDER

(71) Applicant: ERANOVA, Le Bourget du Lac (FR)

(72) Inventors: Philippe Lavoisier, Myans (FR); Ronan Pierre, Pleubian (FR); Maud Benoit, Pleubian (FR)

(73) Assignee: ERANOVA, Le Bourget du Lac (FR)

( * ) Notice: Subject to any disclaimer, the term of this patent is extended or adjusted under 35 U.S.C. 154(b) by 0 days.

(21) Appl. No.: 15/760,901

(22) PCT Filed: Sep. 16, 2016

(86) PCT No.: PCT/EP2016/072020
§ 371 (c)(1),
(2) Date: Mar. 16, 2018

(87) PCT Pub. No.: WO2017/046356
PCT Pub. Date: Mar. 23, 2017

(65) Prior Publication Data
US 2018/0258231 A1 Sep. 13, 2018

(30) Foreign Application Priority Data
Sep. 17, 2015 (FR) ..................... 15 58743

(51) Int. Cl.
| | | |
|---|---|---|
| *C08H 99/00* | (2010.01) | |
| *C08L 99/00* | (2006.01) | |
| *C08B 37/12* | (2006.01) | |
| *C12R 1/89* | (2006.01) | |
| *C07K 14/415* | (2006.01) | |
| *C12N 1/12* | (2006.01) | |

(52) U.S. Cl.
CPC ........... *C08H 99/00* (2013.01); *C08B 37/125* (2013.01); *C08L 99/00* (2013.01); *C07K 14/415* (2013.01); *C08L 2201/06* (2013.01); *C12N 1/12* (2013.01); *C12R 1/89* (2013.01)

(58) Field of Classification Search
None
See application file for complete search history.

(56) References Cited

U.S. PATENT DOCUMENTS

| | | | |
|---|---|---|---|
| 5,779,960 | A | 7/1998 | Berlowitz-Tarrant et al. |
| 2012/0252054 | A1* | 10/2012 | Botsch ................... C12N 9/242 435/29 |
| 2013/0220173 | A1 | 8/2013 | Sharma et al. |

FOREIGN PATENT DOCUMENTS

| | | |
|---|---|---|
| FR | 3 012 817 A1 | 5/2015 |
| WO | 2010/125490 A2 | 11/2010 |
| WO | 2012/114045 A1 | 8/2012 |
| WO | 2014/128411 A1 | 8/2014 |

OTHER PUBLICATIONS

Macler, Plant Physiol., 1986, 82:136-141 (Year: 1986).*
Lahaye, J. Sci. Food Agric., 1991, 54:587-594 (Year: 1991).*
Lu et al., International Journal of Food Science and Technology, 2013, 48: 1352-1358 (Year: 2013).*
Nov. 11, 2016 Search Report issued in International Patent Application No. PCT/EP2016/072020.
Arnold; "Sustainable algal biomass products by cultivation in waste water flows;" 2013; retrieved from http://www.vtt.fi/inf/pdf/technology/2013/T147.pdf on Jul. 12, 2015.
Chiellini et al; "Biodegradable Thermoplastic Composites Based on Polyvinyl Alcohol and Algae;" Biomacromolecules; 2008; vol. 9; pp. 1007-1013.

* cited by examiner

*Primary Examiner* — Allison M Fox
*Assistant Examiner* — Qing Xu
(74) *Attorney, Agent, or Firm* — Oliff PLC; R. Brian Drozd

(57) ABSTRACT

A process for preparing an algal powder containing a reduced content of proteins, a bioplastic composition formed from such a powder, a process for manufacturing a plastic product obtained from such an algal powder and also the plastic product obtained in this way. Process for preparing an algal powder, especially intended for the manufacture of a plastic product, including the successive steps of: culturing and/or harvesting an algal biomass; reducing by at least 10% the intrinsic amount of proteins of the algae, by weight relative to the weight of proteins of the harvested biomass; drying; and reducing to give powder or granules.

8 Claims, No Drawings

PROCESS FOR PREPARING AN ALGAL POWDER CONTAINING A REDUCED CONTENT OF PROTEINS, AND BIOPLASTIC COMPOSITION FORMULATED FROM SUCH A POWDER

The present invention belongs to the technical field of materials formulated from natural matter, more specifically plastic materials, and relates to a process for preparing an algal powder containing a reduced content of proteins, a bioplastic composition formed from such a powder, a process for manufacturing a plastic product obtained from such an algal powder and also the plastic product obtained in this way.

A plastic product is a product obtained from a composition containing polymers, to which are added different additives, such as plasticizers. Conventional plastic is composed of polymers derived from the petroleum industry. However, the exhausting of petroleum resources and environmental conservation have motivated the search for compounds not derived from petroleum, and plastics formulated based on compounds of natural origin are a beneficial alternative to conventional plastics.

Plastic products are often manufactured by extrusion. The starting material which is in the form of granules or of powder is passed into an extruder which makes it possible to continuously produce parts such as profiled elements, cables, tubes, sheets, films, fibres, plates, rods, etc.

Algae are currently considered to be exploitable sources of polymers. They have proved their effectiveness in various fields such as the fields of food, pharmaceuticals, fuel or cosmetics. In addition, the proliferation of algae along coastlines is becoming a worrying, large-scale phenomenon.

Regarding the field of plastic products, algae represents a source of beneficial raw materials due to their richness in polymers.

Bioplastic compositions produced from macroalgae or microalgae are generally produced by grinding dried algal matter, then mixing with other components such as plasticizers. In this regard, mention will be made of the published patent application US 2013/0220173.

Bioplastic compositions based on algae are then generally used in the form of granules, after passage into a screw extruder.

The plastic products that may be manufactured from these granules are injection-moulded, thermoformed, bubble-extruded, or extrusion blow-moulded.

The microalgae or macroalgae used for the preparation of bioplastic compositions are generally green or brown algae. It is advantageous to be able to use them in their entirety, that is to say with all the components of the alga: proteins, polysaccharides, minerals, etc.; indeed, numerous bioplastic compositions are known which are formulated from extracted, purified and concentrated algal polysaccharides. For example, numerous plastic products comprise alginates as components. Such processes are expensive, long and require precise extraction steps.

The compositions produced from whole algae reduced to powder confer reduced mechanical properties on the plastic products formed. These plastic products are relatively brittle. In addition, the algal powders are used as fillers, generally at an amount of approximately at most 15% by weight. In sectors for exploiting algae, it would be advantageous to be able to increase the content of algae in plastic products.

Another major drawback in bioplastic compositions based on microalgae or macroalgae is that they have a strong odour and a very pronounced, for example brown, colour. It is also noted that problems of odour and of colour are accentuated during the manufacture of plastic products, in particular during processes of extrusion, of moulding, of injection moulding, of thermo-compression moulding, etc., of the bioplastic compositions.

In order to overcome this problem, some processes include the addition of compounds able to absorb or mask the odour, such as active carbon, and of dyes. In this case, it is necessary to perform the task of selecting both the origin and the amount of the component to be added in order to obtain stable, effective, and natural mixtures and to avoid any incompatibility between components. The results obtained are not always satisfactory and the task of selection is an additional constraint.

Recent research studies have made it possible to achieve technical advances which make it possible to improve the bioplastic compositions formulated from algal components, especially to increase the content of algal matter in these compositions and to obtain plastic products having good mechanical properties.

In this regard, the French patent application FR 3 012 817 describes bioplastic compositions formulated from an algal component, from plasticizers of natural origin, such as glycerol, and from polymers of plant origin, such as starch. Preferably, the algal component is in the form of an algal residue containing what are referred to as "semi-refined" polysaccharides, since they are not entirely extracted and not purified. Better plasticization of the starch in bioplastic compositions produced from residues containing semi-refined polysaccharides compared to refined, therefore purified, extracts of the same polysaccharides, has been observed.

Moreover, it was demonstrated in the French patent application FR 3 012 817 that by using specific conditions for culturing the algal biomass, it was possible to increase the endogenous starch synthesis. It was also demonstrated that the use of an algal biomass in which the endogenous starch synthesis had been accentuated before the preparation of an algal residue containing semi-refined polysaccharides made it possible to obtain plastic products with advantageous mechanical properties, especially properties of good resistance to breakage. The mechanical properties of these bioplastics produced, due to the richness in starch, are superior to those of bioplastics obtained by simply drying and grinding microalgae or macroalgae.

However, while the bioplastic compositions and bioplastic products described in the abovementioned patent application have good mechanical characteristics, they also have poor odour characteristics and a persistent dark or brown colour, which goes against the transparency or light colour desired in plastic products.

It is within this context that the applicant company carried out research in order to overcome the problems of colour and of odour of bioplastic compositions and bioplastic products obtained from algae.

Macroalgae and microalgae are composed essentially of carbohydrates, of proteins, of pigments and of minerals. Depending on the species and on the harvesting period thereof, the contents of these components may vary widely. For example, depending on the season, algae produce more proteins which constitute their reserves, and which will be used during their period of growth.

During the formation of bioplastics, the materials are subject to high temperatures and to significant shear rates. At such temperatures, the amino acids of the proteins react with the polysaccharides according to a reaction known as the Maillard reaction. The Maillard reaction is a known reaction which has been, and is, the subject of numerous studies in order to attempt to identify all the mechanisms thereof. Numerous works describe the principles thereof in detail which, as a result, will not be described in the present description.

The applicant company has demonstrated that Maillard reactions were also responsible for the phenomena of coloration and the release of undesirable odours during the processes for producing bioplastics, due to the synthesis of aromatic and odorous compounds. It has therefore worked to solve this technical problem.

The aim of the present invention is to overcome the abovementioned drawbacks, and in particular to propose a process making it possible to obtain an algal powder which is able to be used in the preparation of bioplastic compositions and bioplastic products that are devoid of undesirable colour and odour.

Another aim of the invention is to propose such an algal powder which is also able to be used in the preparation of plastic compositions having optimum plasticization characteristics and, in the preparation of plastic products, having optimum mechanical properties, such as resistance to breakage, traction and tension, and elongation at break.

Finally, another aim of the invention is to propose a bioplastic composition and bioplastic products produced from an algal powder according to the invention.

To this end, the invention relates to a process for preparing an algal powder, especially intended for the manufacture of a plastic product, comprising the successive steps of:
culturing and/or harvesting an algal biomass,
reducing by at least 10% the intrinsic amount of proteins of the algae, by weight relative to the weight of proteins of the harvested biomass,
drying,
reducing to give powder or granules.

The reduction in the intrinsic content of proteins in the cells composing the algal biomass makes it possible to reduce the phenomena of Maillard reactions and makes it possible to obtain a powder able to be used for the preparation of bioplastic products and compositions having good characteristics in terms of a reduction in, or even an absence of, undesirable coloration and odours.

Preferentially, the reducing step is a step of reducing by at least 40%, preferentially by at least 70%, more preferentially by at least 75%, the intrinsic amount of proteins of the algae, by weight relative to the weight of proteins of the harvested biomass.

Indeed, the process according to the invention makes it possible to reduce by more than 75% the amount of proteins initially present in the algal biomass. Similarly, it makes it possible to obtain an algal powder having a greatly reduced content of proteins, relative to the total weight of the powder.

According to a preferred embodiment of the invention, reducing the intrinsic amount of proteins of the harvested algae comprises:
the enzymatic hydrolysis of the intrinsic proteins by mixing the harvested algal biomass, preferentially ground, and one or more proteases, then
the separation of a hydrolysate enriched in protein matter and an algal residue.

The process according to the preferred embodiment of the invention consists in carrying out an enzymatic hydrolysis of the proteins of the algae and the separation of the protein matter obtained, which is rich in peptides and amino acids, from an algal residue in which the content of proteins is significantly reduced. The bioplastic compositions produced from this algal residue are colourless or hardly coloured and odourless. The products extruded and injection moulded by transformation of the bioplastic granules are also colourless and odourless. Surprisingly, these products have superior mechanical properties to the plastic products obtained from dried algal powders or algal powders prepared according to a process described in the French patent application FR 3 012 817.

According to such a process of enzymatic hydrolysis, the amount of proteins of the algae may be reduced by at least 40%, preferentially between 40 and 80%, more preferentially between 50 and 75%, by weight relative to the total initial weight of the proteins.

Moreover, the hydrolysates of protein matter recovered have a significant economic value for applications such as applications in cosmetics, fertilizer and nutrition, especially animal nutrition. This exploitation of by-products with a high added value from the process which is the subject of the invention, resulting from this enzymatic treatment, reinforces the economic model of algal culture.

Advantageously, the enzymatic hydrolysis of the proteins is carried out by means of one or more proteases, in particular one or more endopeptidases and/or exopeptidases, of bacterial or fungal origin, such as one or more enzymes obtained from *Bacillus licheniformis*, *Bacillus subtilis*, *Bacillus amyloliquefaciens* or *Aspergillus oryzae*, preferentially from *Bacillus licheniformis*.

Depending on the nature of the enzyme used and/or on the nature of the alga treated, the degree of reduction in the amount of proteins will vary. The enzymes of bacterial or fungal origin used within the context of the present invention are all commercially available. For example, as enzyme obtained from *Bacillus licheniformis*, mention will be made of Alcalase sold by Novozymes. As enzyme of fungal origin obtained from *Aspergillus oryzae*, mention will be made of Flavourzyme, also sold by Novozymes. Generally, the enzyme is added at a concentration of between 0.1 and 10% relative to the weight of proteins to be hydrolysed, preferentially between 0.8 and 3%, more preferentially between 1 and 2%.

According to an advantageous embodiment of the invention, the process also comprises a step of:
depigmenting the algae with or without treatment by a chemical agent, following the step of harvesting an algal biomass and prior to reducing the intrinsic amount of proteins of the harvested algae.

The aim of the depigmentation is to bleach and/or reduce the content of natural pigments, for example of chlorophyll, of the alga.

Natural depigmentation of the algae may be obtained for example by spreading the algae in layers outside any building during the day and then washing them overnight. The steps may be repeated for approximately three days.

For chemical depigmentation, use will be made for example of a chlorinated bleaching agent.

Preferably, the depigmentation will be carried out by alcoholic extraction, by means of one or more steps of maceration of the biomass in solutions of alcohol, advantageously of ethanol.

According to a preferred embodiment of the invention, the process also comprises, directly after the step of reducing the intrinsic amount of proteins of the algae:
a step of destructuring the cell walls of the algae, by mixing the algal residue and a polysaccharide-solubilizing agent, such as a chelating agent or an inorganic acid, preferentially selected from citric acid, citric acid monohydrate, sodium oxalate, hydrochloric acid, sodium carbonate, more preferentially citric acid, heating the mixture to a temperature of between 80 and 100°, preferentially 90° C., for 1 to 4 h, preferentially 2 h, then cooling and concentrating the algal residue, it being understood that said step does not comprise any removal or separation of the organic and inorganic components.

Such a step makes it possible to obtain an extract of what is referred to as "semi-refined" or solubilized polysaccharides. During this step, chelating solubilizing agents, such as citric acid or oxalic acid, capture certain ions present in the cell wall and thereby promote the solubilization of certain ionic polysaccharides and the destructuring of the cell walls. Alternatively, when the solubilizing agent is an inorganic agent such as hydrochloric acid, the latter will also modify the solubility of the polysaccharides, or even partially hydrolyse them, and modify the interactions within the cell wall. They thereby also produce an effect of destructuring of the cell walls.

In the residue obtained, the polysaccharides are predominantly solubilized, but are not separated from the other, non-polysaccharide, constituents of the alga. Indeed, the residue obtained at the end of this step contains all the components of the alga present before its processing, that is to say semi-refined polysaccharides, fibres, and the rest of the protein matter which was not removed in the previous step. There is no extraction/separation/purification of the polysaccharides as in the case of a "refined" polysaccharide extract. This step makes the polysaccharides, especially the cell wall polysaccharides, accessible and functional in comparison to the same polysaccharides contained in cells with structured walls. For this reason, the expression "activated alga" or "step for activating the alga" will also be used in the present application. This step is advantageous in terms of cost and time, since it does not incorporate a total process of extraction of the polysaccharides, especially the cell wall polysaccharides, which is known as a refined process, but rather a process of semi-extraction or semi-refined process.

Advantageously, the step of destructuring the cell walls of the algae comprises the successive steps of:
obtaining a ground algal biomass material,
mixing said ground material and water to obtain a paste,
adding a solubilizing agent, in particular citric acid, to a pH of between 2.5 and 3.5, preferentially 3,
heating the mixture to a temperature of between 80 and 100°, preferentially 90° C., for 1 to 4 h, preferentially 2 h,
cooling to a temperature less than or equal to 45° C.,
concentrating under vacuum at a temperature of between 45 and 50° C.,
adjusting the pH of the residue obtained to a value of between 7 and 8, preferentially 7.7, by means of a base such as sodium hydroxide.

The choice of the polysaccharide-solubilizing agent must take into account the compatibility between this agent and any other compound which will be added in the preparation of the bioplastic compositions, such as plasticizers. The applicants have thus demonstrated that the molecular weight of the solubilizing agent was a dominant factor such that this agent may for example be thermally stabilizing, as will be illustrated below.

According to one embodiment, the process according to the invention also comprises, after the step of reducing the intrinsic amount of proteins of the algae, and, when the process comprises a step of destructuring the cell walls of the algae, directly thereafter, a step of obtaining a paste comprising the steps of:

precipitating by means of alcohol,
separating alcohol and precipitate,
drying the precipitate.

According to a preferred embodiment of the invention, the process also comprises, immediately before the step of obtaining a paste, a step of adding starch to the algal residue, comprising the steps of:
mixing a dispersion of starch and the algal residue ground beforehand,
heating the mixture to a temperature of between 80 and 100° C., for 1 to 3 h,
cooling to a temperature of between 45 and 50° C.

Starch is a biodegradable compound of natural origin which is currently considered to be a raw material of interest for the production of bio-based plastic materials. It may be readily plasticized by means of a plasticizer, such as water or glycerol, and is particularly suited to the manufacture of films.

The starch may be chosen from native starches such as corn starch, wheat starch, potato starch, tapioca starch, pea starch, rice starch or mixtures thereof, or else a starch-derived polymer.

Advantageously, the process comprises a step of culturing algae in conditions flavouring the biosynthesis of starch, said culture comprising setting up an algal biomass in a tank and culturing for four to six weeks, preferentially four weeks, in a seawater culture medium without supplying fertilizers, especially without supplying nitrogen.

An algal biomass containing up to 30%, or even up to 40%, of starch by weight relative to the weight of the biomass may be obtained from culture conditions that promote the synthesis of starch by the alga. Such aquaculture conditions are defined in the scientific paper entitled "Tuning the polysaccharide profile in Ulvacea through controlled tank aquaculture conditions", CEVA, Alg'n'Chem, Montpellier, November 2011, and also the published doctoral thesis entitled "Influence des conditions de culture d'algues marines de l'ordre des Ulvales sur leur croissance et leur composition" [Influence of the conditions for culturing marine algae of the order Ulvales on their growth and composition], 2009. In this thesis, it is established that when algae of the species *Ulvaria obscura* and *Ulva armoricana* are cultured in conditions with depleted medium, their total sugars content increases considerably. This is due to the increase in the glucose content in the tissues, to the detriment of other constituent sugars. Algae subjected to nitrogen limiting start to produce sugars, and especially reserve sugars such as starch (Gómez Pinchetti et al., 1998, Andersen, 2005). Similarly, it is known that starch breakdown is accelerated in darkness, especially when the culture media are enriched in nitrogen (Rosenberg et al., 1982; Williams et al., 1985; Ekman et al., 1991; Rincones et al., 1993; Wiencke et al., 2007). Thus, under controlled culture conditions, that is to say control of the duration of the culture, of the light level and of the enrichment or non-enrichment of the culture medium by means of a fertilizing composition, especially supplementing the medium with nitrogen, it is possible to influence the metabolism of the algae so as to lead to the synthesis of certain compounds. Regarding the increased synthesis of starch by the alga, it has thus been observed that it is useful not to supplement the culture medium with fertilizers, especially with nitrogen. Moreover, the absence of darkness during the culture should be favoured. Nonetheless, in order to make it possible to obtain a strong biomass having a content of starch of up to 40% of the dry matter, the culture conditions may be defined as follows: a first culture phase in the presence of seawater supplemented with fertilizers (Conway's or Walne's composition), so as to promote the growth of the biomass, followed by a culture phase in the presence of seawater not supplemented with fertilizers, especially nitrogen, so as to promote the production of starch by the alga. In a practical manner, the algae are harvested in a nutrient-rich marine environment. This may be, for example, a known zone of proliferation of algae. The algae are then transferred into tanks devoid of nutrients, in which they will then convert proteins into starch, which corresponds to an enrichment of the starch for a loss of protein content. For example, more than 20% (by weight) of glucose is obtained after four days of maturation and nearly 40% after nine days.

According to one embodiment of the invention, the algae are microalgae or macroalgae, preferentially green algae (Chlorophyceae), brown algae (Phaeophyceae) or red algae (Rhodophyceae), more preferentially algae of the genus *Ulva* or of the family Sargassaceae.

By way of example of green algae of the genus *Ulva*, mention will be made of *Ulva armoricana* or *Ulva lactuca*.

The distinction between microalgae and macroalgae is unclear. Algae classed among the macroalgae are those algae for which the vegetative organs are visible to the naked eye, with those of microalgae being visible under a microscope.

The microalgae may for example be selected from Chlorophyceae or diatoms.

The invention further relates to an algal powder obtained by means of a process as described above, and also a bioplastic composition, especially intended for the manufacture of a plastic product, comprising an algal powder obtained by means of a process as described above.

Advantageously, the algal powder according to the invention contains less than 5% of proteins, by weight of proteins relative to the total weight of the powder. Generally, it makes it possible to obtain a powder containing between 1 and 4%, preferentially between 1 and 2% of proteins relative to the total amount of powder.

The process according to the invention thus makes it possible to obtain an algal powder with high added value, given the small amount of proteins in the powder obtained.

Advantageously, the bioplastic composition comprises at least one other component such as a plasticizing compound, a natural polymer, a stabilizer, an antioxidant, an anti-UV agent, a dye, a filler, an agent promoting compatibility between compounds, water or a preservative.

The plasticizers, providing more flexibility and promoting plasticization of the algal powder, were selected from polyols from plant triglycerides such as, for example, triols: glycerol (monoglycerol), diglycerols (diglycerol >90%), polyglycerol-3s (triglycerol >35%), polyglycerol-4s (tri- and tetraglycerol >65%); diols: ethylene glycol, diethylene glycol, triethylene glycol, propylene glycol, (propane-1,2-diol), trimethylene glycol (propane-1,3-diol), butylene glycol (butane-1,3-diol), n-butylene glycol (butane-1,4-diol), 2,3-butylene glycol or secbutylene glycol (butane-2,3-diol); tetraols: erythritol; pentols: xylitol, arabitol, ribitol; hexols: sorbitol, galactitol, mannitol; heptols: volemitol; disaccharide polyols containing nine OH functions: maltitol, isomaltitol, lactitol, and any combination of these compounds.

GMO-free plant diglycerols, such as the product SP-PG3 from SPIGA, were preferentially used. They will moreover be preferred to glycerol, since they migrate less. Indeed, glycerol tends to migrate to the surface of the plastic part produced and tends to impart a greasy appearance on the product, with a loss of mechanical properties. The diglycerol molecule is bulkier than that of glycerol and therefore migrates to a much lesser extent in the polymer matrix. In addition, diglycerols provide better plasticization of the bioplastics. These plasticizers are used at contents of 10% by weight of the algal powder and up to 10% of the bioplastic.

Polymers other than starch may be added and are selected depending on the characteristics that they may provide to the desired plastic product. These may be characteristics of hydrophobicity, transparency, traction resistance, hardness, printability, etc.

Biodegradable thermoplastic polymers are selected from polylactic acid (PLA) (produced by Natureworks), polybutylene succinate (PBS), polybutylene succinate adipate (PBSA) (produced by Showa Denko under the BIONOLLE references, series 1000 (PBS) and 3000 (PBSA)), polybutylene adipate terephthalate (PBAT copolyester) (produced by BASF under the ECOFLEX references, or DuPont under the BIOMAX reference), polyhydroxyalkanoates (PHA) (produced by METABOLIX), polyhydroxybutyrates (PHB), polyhydroxyvalerates (PHV), polyhydroxybutyratehydroxyvalerate copolymers (PHBV), polycaprolactones (PCL) (CAPA, series 6500 and 6800).

Polyvinyl alcohols, or PVA, may be mixed with the algal powder in the compositions of the present invention and reinforce the biodegradability, the properties of transparency and mechanical strength of the finished material and the flexibility, and enable good dispersion of the starches. PVAs will be chosen with molecular weights of between 20 000 and 80 000 Da. Among the commercially available PVAs, mention may be made of the product sold under the trade name CELVOL E 205 by the company Sekishui; 87-90% hydrolyzed, having a molecular weight of between 30 000-70 000 Da and a viscosity of between 4-6 cps at 4%, or the product sold under the trade name MOWIOL 5-88 by the company Kuraray; 87% hydrolyzed, with a molecular weight of approximately 31 000 Da.

Bioplastic compositions derived from bio-based materials may also be produced by mixing the algal powder with polyolefins produced from plant resources such as the polyethylenes derived from sugar cane, such as those from BRASKEM.

Hybrid bioplastic compositions may include algal powders and non-biodegradable and non-bio-based polymers such as polyolefins (polypropylene homopolypropylene (Homo PP) and polypropylene copolymer (PPC), polyethylenes), polystyrenes, polyesters, polyvinyl chloride (PVC), poly(acrylonitrile-co-butadiene-co-styrene (ABS), thermoplastic elastomers such as polyurethanes, styrene block copolymers (SAS, SBS) such as those produced by KRATON polymers LLC, Houston, Tex., ethylene vinyl acetate (EVA), or mixtures thereof.

The bioplastic compositions may also include additives such as anti-UV agents and antioxidants. Among these, mention may be made of the products sold under the trade names Irganox 1010, Irganox B-225, Irganox B-900, irgastab by Ciba specialty chemicals, or Cyanox LTDP by Cytec. These additives are added in amounts which may range up to 0.5% by weight of the total weight of the composition.

As mineral fillers, mention may be made of talc, calcium carbonate, or titanium dioxide (rutile or anatase). These fillers are used to provide whiteness and/or opaqueness to the final plastic product. It is also possible to use carbon black which will give opaqueness and a black colour to the final plastic product.

The bioplastic compositions may also include thermoreactive and/or photoreactive oxo-biodegradable additives which, under the effect of light, temperature, or the combination of these two, will oxidize polyolefins such as polyethylenes and polypropylenes in order to make them biodegradable in the presence of microorganisms. By way of example, such additives are produced by Symphony in the D2W-DG13-15 series.

Odour absorbers may also be added, for an additional action on the problems of odour in the formation of bioplastics, when particularly odorous additives are added, such as vanillin (odour masking agent), or inorganic antimicrobial additives in PE matrices such as masterbatch 9655 from Symphony.

Preferably, the composition comprises between 10 and 60% by weight, preferentially between 15 and 55% by weight, of an algal powder obtained by means of a process as defined above and between 90 and 40% of at least one other component.

The present invention further relates to a process for manufacturing a plastic product which includes a process for preparing an algal powder as defined above.

Advantageously, the process for manufacturing said plastic product also comprises a step of preparing a bioplastic composition from said algal powder.

Further advantageously, the process for manufacturing said plastic product comprises a step of extruding said bioplastic composition to give granules.

Further advantageously, the process for manufacturing said plastic product comprises a step of forming a plastic product by injection moulding, extrusion blow moulding, or sheet die extrusion, of said bioplastic composition.

Finally, the invention relates to a plastic product obtained by such a manufacturing process.

According to a preferred embodiment of the invention, the product is a food film or a non-food film, or a moulded or thermoformed item, such as packaging, for example multilayered or sheet packaging.

The characteristics of the invention, and also others, will become more clearly apparent upon reading the following illustrative and non-restrictive embodiments.

EXAMPLE 1: OBTAINING A CONTROL ALGAL POWDER

Green algae of the species *Ulva Armoricana* were harvested, dried to give flakes at 50° C., then reduced to particles with a mean size of 100 µm in diameter. 2 kg of powder was thus obtained. The composition of the algal powder is given in table 1.

TABLE 1

| Dry matter (DM) | 88.9% dry |
| Starch content | 4.1% dry/crude* |
| Protein content | 14.5% dry/crude |

*% dry/crude: Weight of dry matter of the compound relative to the weight of "crude" dried algae, that is to say without correcting for the percentage of residual moisture still remaining in the dried algae.

It is noted that the starch content is 4.1% dry/crude in this powder.

EXAMPLE 2: OBTAINING AN "ACTIVATED" CONTROL ALGAL POWDER ENRICHED IN STARCH

The process used carried out the following steps in the following order, described in detail in the following example 3:

1—harvesting a biomass of *Ulva Armoricana* green algae, and enrichment under conditions promoting starch synthesis, 2—depigmentation, 3—absent (step of reduction of the intrinsic content of proteins not carried out), 4—destructuring the cell walls by treatment with citric acid (step of activation of the algae), 5—addition of starch (final mixture of 60% dry weight of activated algae and 40% dry weight of starch), 6—precipitation/filtration, 7—drying/reducing to give powder with a mean size of 100 µm in diameter.

Steps 1, 2, 4, 5 and 6 will therefore occur like those of the following example 3.

EXAMPLE 3: OBTAINING AN "ACTIVATED" ALGAL POWDER ACCORDING TO THE INVENTION, DEPROTEINIZED AND ENRICHED IN STARCH

The process used carried out the following steps in the following order, expanded upon below:

1—harvesting a biomass of *Ulva Armoricana* green algae, and culturing under conditions promoting starch synthesis, 2—depigmentation, 3—reducing the intrinsic content of proteins, 4—destructuring the cell walls by treatment with citric acid (step of activation of the algae), 5—adding starch, 6—precipitation/separation, 7—drying and reducing to give powder with a mean size of 100 µm in diameter.

1. Harvesting and Culturing Biomass Under Conditions for Enrichment in Starch:

Ulvas, of the species *Ulva Armoricana* were harvested in France over a period across September and October. During such a period, they have high initial contents of glucose which favour endogenous enrichment in starch. The algae were cultured for 1 month and 4 days in a tank and under nitrogen-deprived conditions. The light conditions were based on the natural light in the months of October and November in Brittany (France). An amount of 18 kg of fresh material was obtained. The algae harvested were frozen under vacuum, without rinsing in freshwater.

15 kg of fresh algae were subsequently defrosted and ground using an URSCHEL-type mill, over a 66896 screen. After defrosting and grinding, 14.65 kg of ground algae were obtained. The following data were measured:

Content of dry matter: 21.38%

Weight of algae (DM: dry matter): 3.13 kg

Protein content: 9.29% dry/dry, i.e. 0.29 kg of proteins

Glucose content (starch): 32.80% dry/dry

The glucose content is representative of the starch content, since the starch is converted into glucose during the quantitative and qualitative analyses. It is noted that the glucose content is 32.80% dry/dry, compared to the glucose content of example 1, of 4.1% dry/crude. There was indeed therefore stimulation and increase in the synthesis of starch by the alga during a culture thereof under conditions favourable to the synthesis of starch by the alga.

2. Depigmentation with Ethanol:

After grinding, carrying out four successive aqueous-ethanolic macerations with the aim of removing as much chlorophyll as possible and of bleaching the alga. Each maceration is carried out by soaking the ground algae for 1 to 3 days in the presence of 25 l of ethanol. At the end of these maceration steps, the mixture is filtered over a cloth having 100 micron diameter pores, and the ground and depigmented algae are recovered. The amount of bleached ulvas obtained is 14.90 kg having a DM of 16.47%, i.e. 2.45 kg dry. The yield by weight of this step is 78%.

The total protein content is determined by the Kjeldhal method (N×6.25). The principle of this method is a multiplication of the inorganic nitrogen content by a mean coefficient which represents the nitrogen richness of the animal or plant proteins. The total protein content is expressed as percentage of proteins (weight of dry matter) relative to the dry weight of the "crude" dried depigmented ulvas, that is to say without correcting for the few percentages of moisture present in the dried alga.

Summary:

Amount of dry matter of the algae at the start of the step: 3.13 kg

Amount of dry matter of the algae at the end of the step: 2.45 kg

Protein content: 10.4% dry/crude, i.e. 0.25 kg of proteins

Starch content: 32.1% dry/crude

3. Reducing the Intrinsic Content of Proteins:

The aim of this step is to hydrolyse the proteins enzymatically and to extract the hydrolysates in basic medium. 13.65 kg of depigmented ulvas were used (DM content of 16.47%), i.e. 2.24 kg dry.

3.1 Aqueous Maceration

Suspension of 13.65 kg of depigmented ulvas resulting from the previous step, i.e. 2.24 kg dry, in 47.8 kg of demineralized water and stirring with Rayneri turbine for 30 minutes (DM 3.57%). Then, addition of 11.68 kg of demineralized water to obtain 3.02% DM.

Maceration overnight at a temperature of 7° C., then static separation over 100 µm sieve. In a second stage, manual pressing of the algal residue remaining on the 100 µm sieve with a 30 µm cloth.

Summary of this sub-step: amount: 57 kg (DM: 0.47%) of filtrate and 14.8 kg (DM: 13.04%) i.e. 1.92 kg dry of algal residue. The intermediate yield by weight of this step is 85%.

3.2. First Extraction with Sodium Hydroxide:

This step promotes extraction and accessibility to the enzyme. It enables the extraction of soluble proteins in order to promote the action of the enzyme specifically on insoluble proteins.

The residue resulting from sub-step 3.1 is taken up (1.92 kg dry) in demineralized water and suspended at 3.5% DM. Next, addition of 30% sodium hydroxide, in a sufficient amount to give a final solution with a concentration of 0.12 M.

Stirring with Rayneri turbine for 1 h 30.

Static separation over 100 µm sieve (drip-draining overnight at room temperature), then manual pressing of the algal residue remaining on the 100 µm sieve with a 30 µm cloth.

Summary of this sub-step: amount: 40.2 kg (DM: 1.04%) of filtrate and 14.7 kg (DM: 12.68%) i.e. 1.86 kg dry of algal residue. The intermediate yield by weight of this step is 96%.

3.3. Enzymatic Hydrolysis with an Alcalase® Protease:

Taking up the algal residue from sub-step 3.2 (1.86 kg dry) in demineralized water for suspension at 3.5% DM, i.e. 47.43 kg of demineralized water. Transfer of the medium into a round-bottomed concentrating vessel then adjustment of the pH to 8.0 with 140 g of 96% sulfuric acid (starting pH 12.3). Stirring using a stirrer at maximum speed, and heating to 55° C. Once at temperature, addition of 3.28 g of Alcalase® enzyme from Novozymes, a protease derived from Bacillus lichenformis (Sigma ref: P4860, ≥2.4 U/g). Generally, the enzyme is added at a concentration of between 0.1 and 10% relative to the dry weight of proteins, preferentially between 0.8 and 3%, more preferentially between 1 and 2%. Stirring overnight (12 h) at 55° C.

3.4. Second Extraction with Sodium Hydroxide:

After cooling to 30° C., adjustment of the pH to 12.0 with 498 g of 30% NaOH (initial pH: 5.23). Static separation over 100 µm sieve then, in a second stage, manual pressing of the algal residues remaining on the 100 µm sieve with a 30 µm cloth.

Summary of this step: amount: 47 kg (DM: 1.97%) of filtrate and 14 kg (DM: 8.90%) i.e. 1.24 kg dry of algal residue. The intermediate yield by weight at this step is 66%.

The filtrate, rich in protein matter (peptides and amino acids), is harvested with a view to subsequent exploitation.

3.5. Rinsing the Algal Residue in Water

Taking up the residue obtained in sub-step 3.4 (1.24 kg dry) and rinsing with demineralized water for suspension at 3% DM, i.e. 27.53 kg of demineralized water added.

Stirring for one hour and separation over 100 µm sieve overnight (no pressing with 30 µm cloth required).

Summary:

Amount of dry matter of the algae at the start of the step: 2.24 kg

Amount of dry matter of the algae at the end of the step: 1.11 kg

Yield by weight: 49%.

Protein content: 5.6% dry/crude, i.e. 0.06 kg of proteins

Starch content: 49.4% dry/crude

The protein content of the algal residue, determined by the Kjeldhal method (N×6.25) is 5.6% dry/crude. The protein content in the residue (5.6% dry/crude) has been reduced by 46% relative to the protein content in the residue from the previous step (10.4% dry/crude).

The final amount of proteins (0.06 kg) has been reduced by 79% by weight, relative to the total starting protein amount (0.29 kg).

Enzymatic Hydrolysis Using Another Enzyme:

Enzymatic hydrolysis of the proteins was carried out, by way of comparison, on 2 kg of biomass in order to check the feasability of the process using other proteases, especially using a protease derived from Aspergillus oryzae and sold under the name Flavourzyme by Sigma. The algal biomass used in this test underwent the same steps as steps 1 to 3 described above. The protein content was reduced by 12% (amount of residual proteins (by weight), relative to the amount of proteins initially present). The colour characteristics are the obtaining of a yellow-green residue like in the case of the use of Alcalase. However, a relatively unsatisfactory odour is noted. Hydrolysis using Alcalase is preferred.

4. Activation of the Algae: Destructuring of the Cell Walls:

As a reminder, the principle is that of destructuring the cell walls by means of a polysaccharide-solubilizing agent, in the present case using a chelating agent, and more specifically that of breaking the bonds, especially the ionic bonds, involving the cell wall polysaccharides, in order to make the cell wall polysaccharides accessible, free, and functional, hence active, without being obliged to extract them by means of precise and refined extraction processes. At the end of this step, the algal residue recovered contains polysaccharides and also all the non-polysaccharide components present before carrying out this step.

The algal residue resulting from step 3 is taken up to be ground in a colloid mill tightened as much as possible in order to have a smooth paste, with addition of 12 kg of water in order to propel the residues and rinse the mill. After grinding, obtaining 26.6 kg (DM: 4.07%) of an algal residue in the form of a thick puree, i.e. 1.08 kg dry.

Transfer of the ground algal residue, i.e 26.6 kg, into a 100 l enameled reactor and addition of 11.4 kg of water to rinse the equipment. In total, 38 kg of ground material (final calculated DM: 2.85%), i.e. 1.08 kg dry, employed for activation by means of a chelating agent: citric acid monohydrate.

The pH is adjusted to 3 with 436.5 g of citric acid monohydrate.

The reaction medium is heated and kept at 90° C. for 2 hours with stirring, then cooled to room temperature (measurement of the pH after cooling: 3.06).

Then, all the medium (algal residue and liquid) is transferred directly into a round-bottomed concentrating vessel and concentrated under vacuum at 45 to 50° C. Approximately 15 litres of water are then eliminated. At this stage, the absence of a separation or filtration step, leading to the elimination of non-polysaccharide compounds, is noted.

22.2 kg, at 6.31% DM, i.e. 1.4 kg dry, of concentrate are recovered.

Neutralization of the concentrate to pH 7.7 with 510 ml of 30% NaOH (DM after neutralization: 6.78%), i.e. 1.5 kg dry.

The intermediate yield regarding this overall activation step is considered to be 100% since no source of loss is identified (1.08 kg+0.487 kg of sodium citrate).

Summary:
Amount of dry matter of the algae at the start of the step: 1.11 kg
Amount of dry matter of the algae at the end of the step: 1.54 kg
Protein content: 4% dry/crude
Starch content: 34.4% dry/crude 5—Addition of a Dispersion of Starch The concentrate of activated algae resulting from the previous step is used at an amount of 22.2 kg (6.78%), i.e. 1.5 kg dry.

A dispersion of starch was prepared so as to obtain a final mixture of 60% by dry weight of activated algae and 40% by dry weight of starch. In order to avoid adding too much water, preparation of a dispersion at approximately 10% starch, i.e. 8.29 kg of water and 1.01 kg of starch. The dispersion of starch is kept at 90° C. for 30 minutes (cooking). The dispersion is highly viscous; 10% is a limit which it is preferable not to exceed.

Transfer of the concentrate of activated algae and of the dispersion of starch at 90° C. into a container enabling stirring using the Rayneri device. Stirring for three hours for thorough mixing, then transfer of the 34 kg of dispersion into 102 l of alcohol (80 l of fresh alcohol and 22 l of recycled 90° alcohol).

Mixing then resting the solution overnight for settling out. Separation of the precipitate over a 30 μm cloth, then manual pressing over a 20 μm cloth. The amount of pressed mixture recovered is 13.1 kg.

Drying in the oven, heating for 5 h at 45° C. The yield of this step is 152%.

Summary:
Amount of dry matter of the algae at the start of the step: 1.5 kg
Amount of dry matter of the algae at the end of the step: 2.3 kg
Protein content: 2.4% dry/crude, i.e. 0.05 kg of proteins
Starch content: 53.4% dry/crude 6. Grinding:

First grinding using Forplex pins takes place, followed by a second grinding on 100 μm Forplex screen.

Amount after grinding: 1.91 kg.

Grinding yield: 83% by weight, associated with the dead volumes of the mills.

The particle size distribution of these ground algae is as follows:

| | |
|---|---|
| >250 μm | 0% |
| 250 μm-160 μm | 0.48% |
| 160 μm-80 μm | 20% |
| 80 μm-40 μm | 75.23% |
| <40 μm | 4.29% |

It is noted that, at the end of the process, an algal powder containing 2.4% of proteins and 53% of starch, as percentage of dry weight relative to the total dry weight of the powder, is obtained.

EXAMPLE 4: BIOPLASTIC COMPOSITIONS

Bioplastic compositions were formulated by mixing the algal powders of examples 1, 2 and 3 with other compounds. Native corn starch is used as control. The compositions formulated are extruded in the form of granules. A total of 49 compositions were formulated. Table 2 below indicates the compositions of the mixtures produced:

TABLE 2

| | Type of powder | | | | | |
|---|---|---|---|---|---|---|
| Formulation No. | Starch (control) | (example 1) | (example 2) | (example 3) | Plasticizer Diglycerol | Polymer PBAT |
| 1 | 35% | | | | 5% | 60% |
| 2 | 45% | | | | 7% | 48% |
| 3 | 55% | | | | 8% | 37% |
| 4 | | 25% | | | 4% | 71% |
| 5 | | 35% | | | 5% | 60% |
| 6 | | 45% | | | 7% | 48% |
| 7 | | 55% | | | 8% | 37% |
| 16 | | | 25% | | 4% | 71% |
| 17 | | | 35% | | 5% | 60% |
| 18 | | | 45% | | 7% | 48% |
| 19 | | | 55% | | 8% | 37% |
| 34 | | | | 25% | 4% | 71% |
| 35 | | | | 35% | 5% | 60% |

TABLE 2-continued

| | | | | |
|---|---|---|---|---|
| 36 | | 45% | 7% | 48% |
| 37 | | 55% | 8% | 37% |

Continuation:

| | | Type of powder | | Plasticizer | Polymer |
|---|---|---|---|---|---|
| Formulation | Starch | Example 1 | Example 2 | Example 3 | Diglycerol | PPC |
| 8 | | 25% | | | 4% | 71% |
| 9 | | 35% | | | 5% | 60% |
| 10 | | 45% | | | 7% | 48% |
| 11 | | 55% | | | 8% | 37% |
| 22 | | | 25% | | 4% | 71% |
| 23 | | | 35% | | 5% | 60% |
| 24 | | | 45% | | 7% | 48% |
| 25 | | | 55% | | 8% | 37% |
| 40 | | | | 25% | 4% | 71% |
| 41 | | | | 35% | 5% | 60% |
| 42 | | | | 45% | 7% | 48% |
| 43 | | | | 55% | 8% | 37% |

Continuation

| | | Type of powder | | Plasticizer | Polymer |
|---|---|---|---|---|---|
| Formulation | Starch | Example 1 | Example 2 | Example 3 | Diglycerol | PBS |
| 12 | | 25% | | | 4% | 71% |
| 13 | | 35% | | | 5% | 60% |
| 14 | | 45% | | | 7% | 48% |
| 15 | | 55% | | | 8% | 37% |
| 28 | | | 25% | | 4% | 71% |
| 29 | | | 35% | | 5% | 60% |
| 30 | | | 45% | | 7% | 48% |
| 31 | | | 55% | | 8% | 37% |
| 46 | | | | 25% | 4% | 71% |
| 47 | | | | 35% | 5% | 60% |
| 48 | | | | 45% | 7% | 48% |
| 49 | | | | 55% | 8% | 37% |

PBAT: (polybutylene adipate terephthalate)
PPC: Polypropylene copolymer
PBS: Polybutylene succinate Formulations 34 to 37, 40 to 43 and 46 to 49 comprise between 25 and 55% by weight relative to the total weight of the compositions of an algal powder obtained according to example 3. These are algae in which the protein content has been reduced, the intrinsic amount of starch has been increased, a supply of starch has been added and the cell wall polysaccharides have been made functional.

EXAMPLE 5: EXTRUSION IN THE FORM OF GRANULES OF THE COMPOSITIONS OF EXAMPLE 4

The extrusion conditions are indicated in table 3

TABLE 3

| Formulation | Extrusion conditions | Injection |
|---|---|---|
| 1-3 | 160, 170, 180° C. - 100 rpm | 170° C. - 8 bar |
| 4-7 | 140, 170, 180° C. - 100 rpm | 170° C. - 8 bar |
| 8-10 | 140, 170, 180° C. - 50 rpm | 170° C. - 8 bar |
| 12-15 | 120, 140, 160° C. - 75 rpm | 160° C. - 8 bar |
| 11 | 140, 190, 200° C. - 50 rpm: extrusion difficult | 180° C. - 8 bar |
| 16 | 120, 140, 160° C. - 50 rpm | 160° C. - 8 bar |
| 17 | 120, 140, 170° C. - 50 rpm | 170° C. - 8 bar |
| 18 | 120, 160, 180° C. - 50 rpm | 180° C. - 8 bar |
| 19 | 130, 160, 180° C. - 50 rpm: extrusion difficult | 180° C. - 8 bar |
| 22-25 | 140, 170, 180° C. - 50 rpm | 170° C. - 8 bar |
| 34-37 | 120, 140, 170° C. - 50 rpm | 170° C. - 8 bar |
| 40-42 | 140, 170, 190° C. - 50 rpm | 180° C. - 8 bar |
| 43 | Extrusion impossible | |

The characteristics of odour, of colour and the mechanical characteristics of the extruded compositions are presented in table 4:

TABLE 4

| | | | | Mechanical properties | | | | |
|---|---|---|---|---|---|---|---|---|
| Formulation | Odour | Colour | Number of test specimens | Modulus, MPa | Threshold stress | Threshold strain | Breaking strength MPa | Breaking strain % |
| 1 | bread | Light beige | 5 | 99 (3) | 10.4 (0.1) | 31.9 (1.5) | 15.6 (1.2) | 387 (225) |
| 2 | bread | beige | 3 | 143 (2) | 9.9 (0.7) | 18 (2) | 12.1 (1.4) | 269 (67) |

TABLE 4-continued

| Formulation | Odour | Colour | Number of test specimens | Modulus, MPa | Threshold stress | Threshold strain | Breaking strength MPa | Breaking strain % |
|---|---|---|---|---|---|---|---|---|
| 3 | bread | beige | 5 | 167 (9) | 10.5 (0.1) | 14.3 (0.5) | 11.7 (0.5) | 186 (35) |
| 4 | Algae | Dusky brown | 3 | 83 (3) | 11.8 (0.2) | 46.4 (2) | 21 (0.3) | 477 (10) |
| 5 | Algae | Dusky brown | 4 | 100 (2) | 11.7 (0.1) | 41.4 (1) | 18.4 (0.5) | 458 (27) |
| 6 | Algae | Dusky brown | 5 | 124 (13) | 11 (0.2) | 36.5 (4) | 13.2 (0.5) | 266 (23) |
| 7 | Algae | Dusky brown | 4 | 164 (30) | 11.8 (0.7) | 24.5 (5) | 12 (1.1) | 93 (53) |
| 8 | Algae | Dusky brown | 5 | 600 (41) | 35.5 (0.5) | 25 (2) | 27.2 (0.4) | 86 (19) |
| 9 | Algae | Dusky brown | 4 | 453 (67) | 33 (2) | 22 (2.3) | 26.5 (1.4) | 55 (19) |
| 10 | Algae | Dusky brown | 3 | 435 (77) | 33 (5) | 23 (3) | 30.3 (4.8) | 35 (6) |
| 11 | Algae | Dusky brown | 1 | 567 | 26 | 18 | 23.9 | 42 |
| 12 | Algae | Dusky brown | 6 | 566 (34) | 32.3 (1.4) | 17.8 (1.5) | 29.9 (1.6) | 29 (5) |
| 13 | Algae | Dusky brown | 4 | 600 (29) | 33.7 (1.8) | 17.7 (1.3) | 32.3 (2) | 28 (1) |
| 14 | Algae | Dusky brown | 4 | 727 (42) | 32.2 (1) | 12.7 (0.7) | 31.5 (1) | 17 (1) |
| 15 | Algae | Dusky brown | 3 | 826 (87) | 26.2 (0.6) | 7.6 (0.6) | 25.6 (0.7) | 10 (0.4) |
| 16 | mild | Light green | 5 | 92 (13) | 11.3 (0.6) | 34.2 (4.4) | 15.5 (0.5) | 171 (32) |
| 17 | mild | Light green | 5 | 139 (10) | 10.4 (0.5) | 23.8 (3) | 12.3 (0.5) | 110 (0.5) |
| 18 | mild | green | 5 | 198 (23) | 9.8 (0.4) | 14.5 (2.1) | 9.7 (0.4) | 56 (13) |
| 19 | mild | Dark green | 3 | 254 (63) | 9.8 (1.7) | 10.3 (7) | 10.6 (0.3) | 30 (26) |
| 22 | mild | semi-transparent | 3 | 418 (16) | 38.1 (1.3) | 25.3 (1.7) | 28.8 (1.4) | 124 (45) |
| 23 | mild | Light beige | 3 | 640 (15) | 32.1 (1.7) | 25 (0.1) | 25.1 (0.9) | 75 (1) |
| 24 | mild | beige | 4 | 713 (74) | 26.6 (1.8) | 23 (2) | 24.3 (2.2) | 67 (28) |
| 25 | mild | Dark beige | 3 | 941 (26) | 21.4 (1) | 17 (0.1) | 21.5 (1) | 24 (0.8) |
| 28 | mild | Light green | 3 | 402 (4) | 30 (1.5) | 32 (2) | 31.5 (1.4) | 232 (0.9) |
| 29 | mild | Light green | 4 | 634 (46) | 24.3 (1.3) | 17 (3) | 25.1 (1.3) | 36 (6) |
| 30 | mild | green | 5 | 903 (106) | 21.8 (1.4) | 6 (1.3) | 21.6 (1.4) | 6 (1.3) |
| 31 | mild | Dark green | 3 | 1215 (92) | 17.1 (0.5) | 3.4 (04) | 17.1 (0.5) | 3.4 (0.4) |
| 34 | none | Very light beige | 4 | 89 (6) | 10.6 (0.2) | 71 (14) | 16.2 (0.6) | 355 (34) |
| 35 | none | Light beige | 3 | 134 (5) | 9.6 (04) | 34 (6) | 11.4 (0.3) | 169 (64) |
| 36 | none | beige | 3 | 174 (5) | 8.6 (0.2) | 22.5 (2.4) | 9.6 (0.1) | 143 (45) |
| 37 | none | beige | 4 | 350 (78) | 10.4 (05) | 9.3 (2.3) | 9.4 (0.9) | 28 (8) |
| 40 | none | semi-transparent | 5 | 512 (92) | 35.1 (3) | 27 (1) | 30.8 (1.2) | 389 (15) |
| 41 | none | Light beige | 3 | 582 (84) | 28.3 (2.6) | 24 (2) | 24.4 (1) | 66 (22) |
| 42 | none | Light beige | 3 | 765 (94) | 23.8 (1) | 24 (4) | 21.9 (1) | 69 (20) |
| 46 | none | Light beige | 4 | 403 (38) | 26.6 (7) | 32 (3) | 30.3 (0.8) | 160 (22) |
| 47 | none | Light beige | 4 | 555 (59) | 21.8 (1) | 19 (3) | 22.8 (1.1) | 66 (16) |
| 48 | none | Light beige | 4 | 836 (96) | 20.7 (0.9) | 7.5 (1.4) | 20.5 (1.1) | 15 (3) |
| 49 | none | Light beige | 3 | 1308 (37) | 19.2 (07) | 3.5 (0.2) | 19.2 (0.6) | 3.5 (0.2) |

The extruded products obtained with the bioplastic compositions 34-37, 40-43, 46-49, containing algal powders according to the invention (example 3) do not give off any bothersome, nauseating or unpleasant odour.

The bioplastic compositions 16-19, 22-25, 28-32, containing algal powders according to example 2, which were prepared according to a process identical to that of example 3 but without the step of reducing the protein content, have a mild odour.

The extruded products obtained with the bioplastic compositions developed from the native starch powder (compositions 1-3) and those developed from algae simply reduced to powder of example 1 (formulations 4-7, 8-11, 12-15), without any treatment, have, respectively, an odour of bread and a strong algae odour.

The process according to the invention is therefore effective in suppressing the odour phenomena.

Regarding colour, the extruded products obtained from algae simply reduced to powder of example 1 (formulations 4-7, 8-11, 12-15) have dusky brown colours. Such colours do not make them usable in the manufacture of the majority of plastic products.

The extruded products obtained with the bioplastic compositions 16-19, 22-25 and 28-31, containing algal powders according to example 2, have light to dark beige colours or light to dark green colours.

Only the compositions 22 and 40 made it possible to obtain a semi-transparent colour. In these formulations, the content of algae is lower than in the compositions 23-25 and 41-43. The polymer is PPC.

In formulation 34, which has the same amount of algae, the colour is a very light beige but less transparent, and the polymer is PBAT. The bioplastic compositions 34-37 and 40-43 will give plastic products for which the colours will not be readily predictable. The addition of a polymer such as PPC is recommended.

The extruded products obtained with the bioplastic compositions 34-37 and 40-43, containing algal powders according to example 3, have light beige colours or are semi-transparent. The formulation 37, containing 55% by weight of algal powder according to the invention, made it possible to obtain a beige extruded product, which is acceptable. Indeed, during the formation of films, the products are stretched and the final colour obtained will depend on the thickness of the film.

Here again, it is noted that the polymer PPC is effective to accentuate transparency.

Among the formulations using PBAT as polymer, it will be noted that the compositions 34-36, developed from algal powders with a reduced protein content, have lower moduli of elasticity than the moduli of the other compositions and much higher breaking strains than with algal powders which have not been deproteinized (16-18). The materials are therefore more flexible with better deformation.

In the formulations using PBS as polymer, it will be noted that the compositions 47-48 with algal powder containing a reduced protein content, have lower moduli of elasticity and much higher breaking strains than with algal powders which have not been deproteinized (28-30); the materials are therefore more flexible with better deformation.

Moreover, the materials with PBS and with the same contents of algae are however more rigid and less deformable than the formulations with PBAT.

In the formulations using PPC, it will be noted that the compositions (40-42), with algal powder containing a reduced protein content, have moduli of elasticity and breaking strains which are equivalent to the algal powders which have not been deproteinized (22-25). The materials incorporating PPC are however more rigid and less deformable than the formulations incorporating PBAT.

EXAMPLE 6: BIOPLASTIC COMPOSITIONS FORMULATED FROM ALGAL POWDERS OBTAINED BY A PROCESS ACCORDING TO THE INVENTION USING ANTI-UV AGENTS, ANTIOXIDANTS, AND ANTI-ODOUR AGENTS

Bioplastic compositions were formulated by mixing the algal powders from examples 2 and 3, PBAT and anti-UV agents, antioxidants and anti-odour agents. In total, four compositions were formulated containing 40% of algal powder.

Table 5 below indicates the compositions of the mixtures produced:

TABLE 5

| Polymer | Algae Ex. 2 | Algae Ex. 3 | Diglycerol | PBAT | PPC | PBS | irgafos 168 | irganox 1076 | 96522 |
|---|---|---|---|---|---|---|---|---|---|
| PBAT | | | | | | | | | |
| 62 | 40% | | 10% | 50% | | | 0.20% | 0.20% | |
| 63 | 40% | | 10% | 50% | | | 0.20% | 0.20% | 0.40% |
| PBAT | | | | | | | | | |
| 64 | | 40% | 10% | 50% | | | 0.20% | 0.20% | |
| 65 | | 40% | 10% | 50% | | | 0.20% | 0.20% | 0.40% |

The extrusion conditions were 120, 140, 170° C.-50 rpm

And the injection conditions were 170° C.-8 bar.

Compositions 64 and 65 are less coloured and odourless compared to formulation 62. Formulation 63 is more coloured but the odour is improved compared to formulation 62.

The addition of antioxidant and anti-UV agent improves the colour compared to the compositions of example 4.

The mechanical properties obtained are as follows (Table 6)

TABLE 6

| Composition | Modulus, MPa | Threshold stress | Threshold strain | Breaking strength MPa | Breaking strain % |
|---|---|---|---|---|---|
| 62 | 150 (6) | 10.1 (0.7) | 21.7 (0.5) | 11 (0.8) | 70 (26) |
| 63 | 196 (5) | 10.9 (1.5) | 15 (5.5) | 11.7 (0.7) | 40 (7) |
| 64 | 204 (15) | 11.3 (0.9) | 18 (0.6) | 11.2 (1.1) | 40 (6) |
| 65 | 232 (22) | 12 (05) | 17.2 (0.4) | 11.3 (0.5) | 39 (3) |

EXAMPLE 7: BIOPLASTIC COMPOSITIONS FORMULATED FROM ALGAL POWDERS OBTAINED BY A PROCESS ACCORDING TO THE INVENTION USING ANOTHER CHELATING AGENT IN THE STEP FOR DESTRUCTURING THE CELL WALLS

The steps of the process according to example 3 were carried out with, in step 4, the following chelating agents: sodium oxalate, sodium carbonate and sodium chloride. The algal powders were mixed with plasticizers and polymers. The molar mass of each mixture was measured. The results are as follows:

a) with sodium oxalate: 570 000 g/mol,
b) with sodium carbonate: 600 000 g/mol,
c) with sodium chloride: 474 000 g/mol,
d) with citric acid: 295 000 g/mol.

The molar mass is halved with citric acid.

Thermal stability tests were also carried out. The 4 products were kept for 3 days at 150° C.:
  with sodium oxalate, sodium chloride and sodium carbonate: the materials are burnt, with strong caramel odours,
  with citric acid: the colour remains light yellow.

Citric acid is therefore preferred, because it limits the problems of compatibility with the other compounds. Indeed, the molecular weight was identified, within the context of the present invention, as being a dominant factor for obtaining a good mixture of the polymers, algae, and other compounds. Moreover, it is advisable to give preference to an activating agent which may also be a thermal stabilizer, such as citric acid.

The invention claimed is:

1. A process for preparing an algal powder, comprising the successive steps of:
  (a) harvesting algae;
  (b) culturing the algae in conditions favoring the biosynthesis of starch, said culturing comprising setting up the algae in a tank and culturing for four to six weeks in a seawater culture medium without supplying fertilizers, and without supplying nitrogen;
  (c) depigmenting the algae in the presence of ethanol;
  (d) reducing by at least 75% the amount of intrinsic proteins of the depigmented algae by enzymatic hydrolysis of the intrinsic proteins, the reducing step (d) comprising:
    (d1) macerating over night the depigmented algae in water, filtering the macerated algae to generate a first algal residue, and recovery of the first algal residue,
    (d2) mixing the recovered first algae residue with a sodium hydroxide solution to produce a mixed algae, filtering the mixed algae to generate a second algal residue, and recovery of the second algal residue, (d3) mixing the recovered second algae residue and *Bacillus licheniformis* as a source of one or more proteases to hydrolyze the intrinsic proteins, then (d4) separating a hydrolysate enriched in peptides and/or amino acids from the hydrolyzed second algal residue to generate a third algal residue, and recovery of the third algae residue;

(e) destructuring the cell walls of the recovered third algal residue by mixing the third algae residue with a chelating agent and water, heating the mixture to a temperature of between 80° C. and 100° C., to generate a fourth algal residue, then cooling and concentrating the fourth algal residue by elimination of water;

(f) adding starch to the concentrated fourth algal residue to form a dispersion of the starch and the concentrated fourth algal residue, (g) drying an algal material derived from the dispersion, and (h) reducing the dried material of the step (g) to give powder or granules, thereby obtaining the algal powder.

2. The process according to claim 1, further comprising adjusting the pH of the concentrated fourth algal residue before adding the starch to the concentrated fourth algal residue; mixing the dispersion of the starch and the concentrated fourth algal residue generated in the step (f); heating the mixed dispersion to a temperature of between 80° C. and 100° C. for 1 to 3 hours; cooling to a temperature of between 45° C. and 50° C., thereby providing the algal material derived from the dispersion.

3. The process according to claim 1, wherein the algae are microalgae or macroalgae.

4. The process according to claim 1, wherein the chelating agent is citric acid.

5. The process for preparing an algal powder according to claim 1, wherein said step of destructuring the cell walls further comprises a step of adjusting the pH of the mixture of the third algae residue, the chelating agent, and water to a pH between 2.5 and 3.5 before the mixture is subjected to the heating, wherein the mixture is heated at a temperature between 80° C. and 100° C. for 1 to 4 hours, and then cooled to a temperature less than or equal to 45° C.; and a step of neutralizing the pH of the concentrated fourth algal residue to between 7 and 8 by means of a base, before the starch is added to the concentrated fourth algal residue.

6. The process according to claim 5, wherein the base is sodium hydroxide.

7. A process for manufacturing a plastic product, comprising the steps (a)-(h) for preparing an algal powder, as described in claim 1, and further steps of preparing a bioplastic composition from the algal powder, and extruding said composition to generate granules.

8. The process for manufacturing a plastic product according to claim 7, further comprising a step of forming the plastic product by injection moulding, extrusion blow moulding, or sheet die extrusion of said bioplastic composition.

* * * * *